United States Patent [19]
Farahi et al.

[11] Patent Number: 5,920,390
[45] Date of Patent: Jul. 6, 1999

[54] FIBEROPTIC INTERFEROMETER AND ASSOCIATED METHOD FOR ANALYZING TISSUE

[75] Inventors: Faramarz Farahi, Concord; Mohammad Yasin Akhtar Raja; Robert Splinter, both of Charlotte, all of N.C.

[73] Assignees: University of North Carolina; Charlotte-Mecklenburg Hospital Authority, both of Charlotte, N.C.

[21] Appl. No.: 08/882,848

[22] Filed: Jun. 26, 1997

[51] Int. Cl.$^6$ ........................................................ G01B 9/02
[52] U.S. Cl. ............................................. 356/345; 356/359
[58] Field of Search ................................... 356/34.5, 359, 356/360; 600/473, 342, 476; 250/227.27

[56] References Cited

U.S. PATENT DOCUMENTS

| | | | |
|---|---|---|---|
| 4,228,804 | 10/1980 | Holasek et al. . | |
| 4,315,514 | 2/1982 | Drewes et al. . | |
| 4,873,651 | 10/1989 | Raviv | 356/375 |
| 5,202,745 | 4/1993 | Sorin et al. | 356/351 |
| 5,203,339 | 4/1993 | Knüttel et al. | 356/345 |
| 5,231,464 | 7/1993 | Ichimura et al. | 356/345 |
| 5,321,501 | 6/1994 | Swanson et al. | 356/345 |
| 5,383,467 | 1/1995 | Auer et al. | 600/342 |
| 5,434,669 | 7/1995 | Tabata et al. | 356/345 |
| 5,459,570 | 10/1995 | Swanson et al. | 356/345 |
| 5,491,524 | 2/1996 | Hellmuth et al. | 351/212 |
| 5,491,552 | 2/1996 | Knüttel | 356/351 |
| 5,493,109 | 2/1996 | Wei et al. | 250/201.3 |
| 5,570,182 | 10/1996 | Nathel et al. | 356/345 |
| 5,710,630 | 1/1998 | Essenpreis et al. | 356/345 |
| 5,716,324 | 2/1998 | Toida | 356/345 |

OTHER PUBLICATIONS

Radiation and Environmental Biophysics—J. Eichler, J. Knof, and H. Lenz—Measurements on the Depth of Penetration of Light (0.35–1.0 $\mu$m) in Tissue—1977—pp. 239–242.

Phys. Med. Biol.—J B Dawson, D J Barker, D J Ellis, E Grassam, J A Cotterill, G W Fisher, and J W Feather—A theoretical and experimental study of light absorption and scattering by in vivo skin—Jan. 29, 1980—vol. 25 No. 4, 695–709.

Journal of Investigative Dermatology—R. Rox Anderson, B.S. and John A. Parrish M.D.—The Optics of Human Skin—1981—77:13–19.

Lasers in Surgery and Medicine—Martin J.C. van Gemert, PhD, A.J. Welch, PhD, and Alpesh P. Amin, BSc—Is There An Optimal Laser Treatment for Port Wine Stains?—1986—6:76–83.

Lasers in Surgery and Medicine—Marleen Keijzer, MSc, Steven L. Jacques, PhD, Scott A. Prahl, PhD, and Ashley J. Welch, PhD—Light Distributions in Artery Tissue: Monte Carlo Simulations for Finite–Diameter Laser Beams—1989—9:148–154.

(List continued on next page.)

*Primary Examiner*—Robert Kim
*Attorney, Agent, or Firm*—Alston & Bird LLP

[57] ABSTRACT

The fiberoptic interferometer includes a broadband light source which is selected to illuminate tissue of predetermined organ with light having a wavelength within a predetermined range of wavelengths. Within the predetermined range of wavelengths, the attenuation characteristics of tissue of the predetermined organ define a region of minimum attenuation upon illumination with light having a first wavelength. As a result, the fiberoptic interferometer can precisely determine the optical properties of the tissue and can therefore identify the tissue by comparing the interferometric signal produced upon illumination of the tissue sample with predetermined interferometric signals corresponding to illumination of different types of tissue of the predetermined organ with light having the first wavelength. The fiberoptic interferometer can also include a light source which includes wavelength selection means for controllably selecting the predetermined wavelength of light emitted by the light source. Thus, the optical properties of the tissue can be analyzed at the different wavelengths emitted by the light source to individually determine the optimum wavelength of light for subsequent treatment of the tissue.

16 Claims, 4 Drawing Sheets

OTHER PUBLICATIONS

Science—Huang et al.—Optical Coherence Tomography—Nov. 22, 1991, vol. 254, pp. 1178–1181.

Lasers in Surgery and Medicine—Robert Splinter et al.—Optical Properties of Normal, Diseased and Laser Photocoagulated Myocardium at the Nd: YAG Wavelength—1991—11:117–124.

Med. Phys. 19 (4)—Thomas J. Farrell, Michael S. Patterson, and Brian Wilson—A diffusion theory model of spatially resolved, steady–state diffuse reflectance for the noninvasive determination of tissue optical properties in vivo—Jul./Aug. 1992—pp. 879–888.

Lasers in the Life Sciences 6(1), Robert Splinter et al.—Monitoring Tissue Optical Characteristics in–situ Using a CCD Camera—1994—pp. 15–25.

Biomechanics, Rehabilitation, Electrical Phenomena, Biomaterials (Part 3 of 3)—Scott Shukes et al.—Exploring the Optical Window of Myocardial Tissue for Localized Laser Ablation of Ventricular Tachycardia—Oct. 28–31, 1993—pp. 1602–1603.

Lasers in Medical Science—Robert Splinter et al.—Computer Simulated Light Distributions in Myocardial Tissues at the Nd–YAG Wavelength of 1064 nm—1993—8:15–21.

Applied Optics—Robert Splinter et al.—Myocardial temperature distribution under cw Nd:YAG laser irradiation in in vitro and in vivo situations: theory and experiment—Jan. 20, 1995—vol. 34 No. 3, pp. 391–399.

Progress in Biomedical Optics—Scott Shukes et al.—Proceedings of Biomedical Optoelectronic Instrumentation—Feb. 7–9, 1995, vol. 2396 pp. 151–156.

Lasers in Surgery and Medicine—Norman S. Nishloka, MD—Applications of Lasers in Gastroenterology—May 3, 1995, 16:205–214.

Presentation SPIE—The International Society for Optical Engineering—Scott Shukes et al.—Feb. 7, 1995.

SPIE—The International Society for Optical Engineering—Robert Splinter et al.—Lasers in Surgery: Advanced Characterization, Therapeutics, and Systems VI—Jan. 27–30, 1996—vol. 2671 pp. 125–131.

SPIE—The International Society for Optical Engineering—Robert Splinter et al.—CIS Selected Papers, Coherence–Domain Methods in Biomedical Optics—Aug. '96—vol. 2732, pp. 242–250.

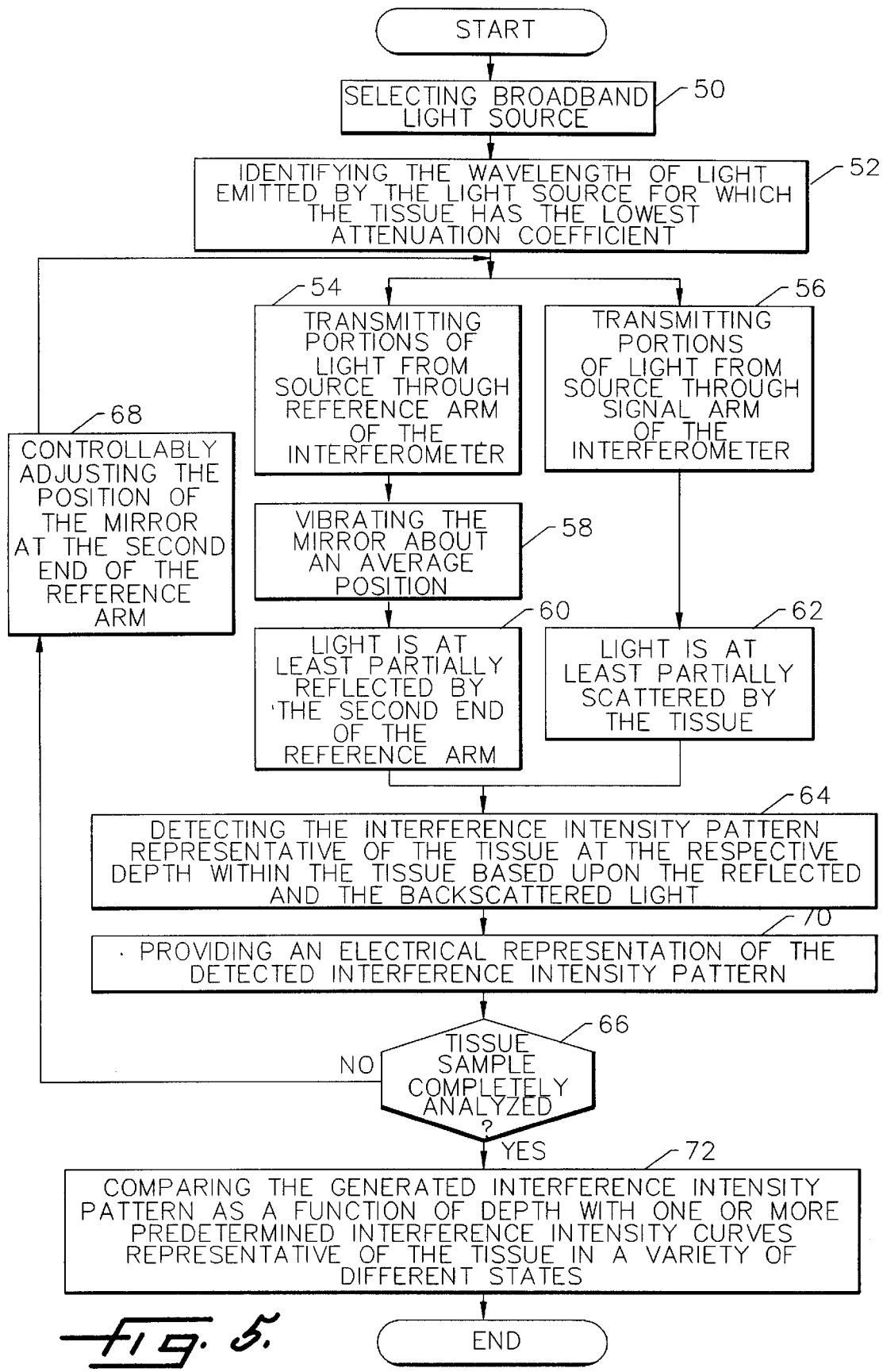

FIBEROPTIC INTERFEROMETER AND ASSOCIATED METHOD FOR ANALYZING TISSUE

FIELD OF THE INVENTION

The present invention is directed generally to broadband fiberoptic interferometry and, more specifically, to a fiberoptic interferometer and an associated method for analyzing the optical properties of tissue of a predetermined organ.

BACKGROUND OF THE INVENTION

Laser treatment is increasingly being used for both experimental and clinical medical purposes. For example, lasers are often employed for photocoagulation or to treat heart ailments, various cancers, etc. The success of such laser treatments depend upon the manner in which the light emitted by the laser and the tissue interact, such as by heating the tissue. As explained in Splinter, et al., "Tissue Diagnostics by Depth Profiling of Optical Characteristics Using Broadband Fiber-Optic Interferometry", Coherence-Domain Methods in Biomedical Optics, SPIE Vol. 2732, pp. 242–50 (August 1996), the manner in which the light emitted by the laser interacts with the tissue depends, in large part, upon the optical properties, such as the absorption and scattering coefficients, of the tissue at the particular wavelength of light with which the tissue is illuminated. In order for subsurface laser treatments to be effective, an optical window must be defined based upon the light-tissue interaction which identifies one or more wavelengths of light for which the tissue has a relatively high optical penetration, thereby efficiently providing subsurface tissues with the required dosage of light to cause the desired photochemical reaction, such as photocoagulation or other photochemical reactions.

In most instances, biological tissues are highly scattering with the particular optical properties, i.e., the scattering and absorption properties, depending on the tissue and the pathological condition of the tissue at the irradiation wavelength. Color and composition of the tissue to be treated can sometimes provide evidence of the optical and thermal properties of the tissue. However, while the optical properties differ for different tissues and for different pathological tissue conditions, these different optical properties are not always distinguishable by visual examination of the tissue.

Since tissue responds differently to light of different wavelengths, the various medical procedures which employ laser illumination can be enhanced by properly identifying the tissue and by thereafter selecting the proper wavelength of light for optimally treating the tissue. The tissue can then be illuminated by light of the proper wavelength to effectively treat the tissue to desired depths.

To more accurately identify tissue samples, a variety of optical coherence tomography techniques have been developed. For example, U.S. Pat. No. 5,459,570 to Swanson, et al., and an article entitled "Optical Coherence Tomography" by Huang et al. which appeared in *Science*, Reprint Series, Vol. 254, pp. 1178–81 (Nov. 22, 1991), describe optical coherence domain reflectometers for generating images of tissue samples. As described by these references, an optical coherence domain reflectometer includes an optical source, a reference arm and a sample arm. The optical source may be a super luminescent diode having a short coherence length which emits light that is coupled to the reference arm and the sample arm of the reflectometer. The tissue sample is placed in the sample arm to scatter and reflect the light propagating therethrough. In contrast, a reference mirror is placed in the reference arm to reflect the light transmitted therethrough. The reference mirror can be translated or moved, such as with a stepper motor, in order to vary the length of the reference arm.

The optical coherence domain reflectometers described by these references also include a detector for receiving the signals returned by the reference and signal arms, including the signals which have been reflected and scattered by the tissue sample and the light reflected from the reference mirror. Based upon the interference pattern created by returning signals, the optical coherence domain reflectometers can identify different layers or boundaries within the tissue. See also U.S. Pat. No. 5,321,501 to Swanson, et al., which describes another optical coherence domain reflectometer.

Nonetheless, optical coherence tomography techniques suffer from several deficiencies. For example, optical coherence tomography techniques typically analyze reflections from boundary layers, such as the boundary layer between two different types of tissue. As a result, optical coherence tomography techniques do not generally analyze signals reflected and/or scattered from within a homogeneous tissue layer which may require the subsequent laser treatment. In addition, optical coherence tomography techniques commonly illuminate a tissue sample with light of a single wavelength or a single band of wavelengths. Thus, optical coherence tomography techniques do not typically determine variations in the optical properties of the tissue sample as the tissue sample is illuminated by light of different wavelengths.

As further explained in Splinter, et al., "Monitoring Tissue Optical Characteristics in-situ using a CCD Camera", Lasers in the Life Sciences, Vol. 6(1), pp. 15–25 (1994), the response of biological media or tissue to illumination can be compared to computer simulations, such as Monte Carlo simulations, to identify not only the tissue itself, but also the pathological condition of the tissue. For example, the Splinter article describes a method and an associated apparatus for determining the optical characteristics of a tissue sample in situ so as to thereby identify the ideal laser dosimetry for tissue photocoagulation. According to this method, a laser beam is delivered to a tissue sample by an optical fiber. A CCD camera is also trained on the illuminated tissue sample so as to detect backscattered radiation. The detected backscatter can then be compared to Monte Carlo computer models which simulate backscatter from tissue samples having known optical parameters in order to determine the optical characteristics of the tissue sample. While the technique described by this Splinter article can identify a number of different types of tissue, modern laser treatments are demanding even greater accuracy with respect to the identification of the optical properties of a tissue sample upon illumination with light of different wavelengths and at different depths within the tissue sample.

SUMMARY OF THE INVENTION

To more accurately analyze tissue of a predetermined organ, a fiberoptic interferometer is provided which includes a broadband light source for providing light having a wavelength within a predetermined range of wavelengths. Within the predetermined range of wavelengths, the attenuation characteristics of tissue of the predetermined organ define a region of minimum attenuation upon illumination with light having a first wavelength. The fiberoptic interferometer also preferably includes means for comparing an interferometric signal representative of the optical properties of the tissue sample with predetermined interferometric signals corresponding to illumination of different types of tissue of the predetermined organ with light having the first wavelength. As a result, the fiberoptic interferometer can more precisely determine the optical properties and, therefore, the type of the tissue sample since the signals which have been least attenuated by the tissue are utilized during the analysis process.

The fiberoptic interferometer of another advantageous embodiment includes a light source which includes wavelength selection means for controllably selecting the predetermined wavelength of light emitted by the light source. Thus, the optical properties of the tissue can be analyzed at each of the different wavelengths emitted by the light source to determine the optimum wavelength of light for subsequent treatment of the tissue.

According to either embodiment, the interferometer includes a reference arm having a first end disposed in optical communication with the broadband light source and an at least partially reflective second end, such as a mirror. The interferometer also includes a signal arm having a first end disposed in optical communication with the broadband light source and a second end disposed in optical communication with the tissue such that a portion of the light provided by the broadband light source illuminates the tissue and is at least partially scattered thereby. Further, the interferometer includes a detector disposed in optical communication with the first ends of both the reference arm and the signal arm for receiving an interferometric signal representative of the tissue. The interferometric signal received by the detector is based upon light reflected by the at least partially reflective second end of the reference arm and light scattered by the tissue. The detector, in turn, provides an electrical representation of the interferometric signal.

The fiberoptic interferometer and, more particularly, the comparing means then compares the interferometric signal received by the detector with predetermined interferometric signals corresponding to illumination of different types of tissue of the predetermined organ with light having the first wavelength. For example, the comparing means can compare the interferometric signal received by the detector with predetermined interferometric signals corresponding to illumination of normal, aneurysm and coagulated tissue of the predetermined organ with light having the first wavelength. By identifying the predetermined interferometric signal which most closely matches the interferometric signal received by the detector, the comparing means can accurately determine the type of the tissue, such as normal, aneurysm or coagulated tissue. By analyzing the interferometric signal received by the detector for light having the first wavelength, the fiberoptic interferometer of the present invention can more precisely determine the optical properties and, in turn, the type or state of the tissue sample since light having the first wavelength is attenuated to a lesser degree than light having other wavelengths, thereby providing a stronger or more intense signal for detection and analysis.

Advantageously, the interferometer further includes mirror positioning means for controllably adjusting the position of the mirror relative to the first end of said reference arm such that the spacing therebetween is correspondingly varied. Thus, the interferometric signal received by the detector and the corresponding electrical signal provided by the detector is a function of depth within the tissue. In particular, the interferometric signal received by the detector is representative of the tissue at a number of different depths since it is based upon light reflected by the mirror and light scattered by the tissue at different depths therein. In addition, the interferometer can include vibration means for vibrating the mirror about an average position to reduce the ambient background noise superimposed upon the interferometric signal.

Therefore, the fiberoptic interferometer of the present invention analyzes the optical properties of tissue at a variety of depths within the tissue and not just at the boundary layers of the tissue. In addition, the fiberoptic interferometer precisely determines the optical properties of the tissue by illuminating the tissue with a broadband light source and by analyzing the resulting interferometric signal at the wavelength of light which is least attenuated by the tissue and which therefore contributes most to the backscattered light signal. Furthermore, the fiberoptic interferometer can determine the optical properties of the tissue based upon illumination by broadband light sources of a number of different center wavelengths, thereby permitting the subsequent laser treatment to be optimized by irradiating the tissue with light having a wavelength at which the tissue has the desired optical properties, such as high absorption for laser heating treatments.

BRIEF DESCRIPTION OF THE DRAWINGS

FIG. 5 is a block diagram illustrating the operations performed by a fiberoptic interferometer and associated method of analyzing a tissue sample according to one embodiment of the present invention.

DETAILED DESCRIPTION OF THE PREFERRED EMBODIMENT

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
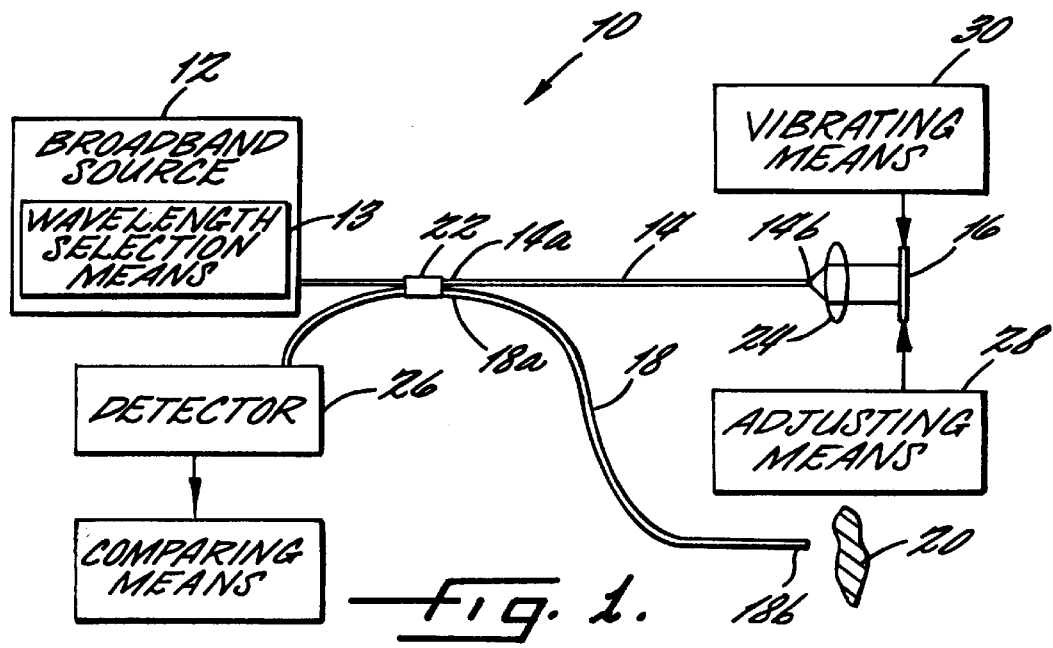
FIG. 1 is a schematic view of a fiberoptic interferometer of one embodiment of the present invention.

Referring first to FIG. 1, a fiberoptic interferometer 10 is shown which incorporates the teachings of this invention. The fiberoptic interferometer includes a broadband source 12, such as a diode, and, more particularly, a super luminescence diode (SLD), for providing light having a wavelength within a predetermined range of wavelengths, such as 780 nm to 830 nm, for example. Typically, the broadband light source 12 of the interferometer of the present invention irradiates a tissue sample 20 with light having the predetermined range of wavelengths. As shown in FIG. 1, however, the broadband light source of one embodiment can include wavelength selection means 13 for controllably selecting the wavelength of light emitted thereby. For example, the wavelength selection means can include one or more filters, downstream of the light source, for selectively passing light of only certain wavelengths. Alternatively, the broadband light source of this embodiment can be a tunable light source, such as a tunable laser. The tissue sample 20 can therefore be analyzed at each of a number of different wavelengths of light in order to determine the optical properties of the tissue sample in response to illumination with light of each respective wavelength. Based on this analysis, any subsequent treatment of the tissue by means of laser irradiation can be optimized by irradiating the tissue with light having a wavelenth at which the optical properties of the tissue promote the desired treatment.

The interferometer 10 also includes a reference arm 14 having a first end 14a disposed in optical communication with the broadband light source 12 and an at least partially reflective second end 14b. Typically, the at least partially reflective second end of the reference arm includes or is formed by a mirror 16. The interferometer also includes a signal arm 18 having a first end 18a disposed in optical communication with the broadband light source and a second end 18a disposed in optical communication with a sample of tissue 20. The reference and signal arms of the fiberoptic interferometer are formed by optical fibers and, more preferably, single mode optical fibers.

Typically, the tissue 20 to be analyzed according to the present invention is of a predetermined organ. For example, the tissue sample may be heart tissue, liver tissue, skin tissue, etc. Even though the tissue is of a predetermined organ, the type or state of the tissue, such as normal, coagulated, aneurysm or fat, is typically unknown, particularly at subsurface depths within the tissue sample. Thus, the fiberoptic interferometer 10 of the present invention analyzes the tissue sample to determine the optical properties and, in turn, the type or state of the tissue sample. By determining the optical properties of the tissue, such as heart tissue, for example, the fiberoptic interferometer can determine or identify, at various depths within the tissue, if the tissue is normal heart tissue, coagulated heart tissue, heart aneurysm tissue or fat. Based on this determination, any subsequent laser treatment can irradiate the tissue with light having a wavelength selected to optimize the resulting treatment.

As also shown in FIG. 1, the light emitted by the broadband light source 12 is typically collimated and thereafter split by an optical coupler 22. The optical coupler provides a portion of the collimated light to the first end 14a of the reference arm 14 for subsequent reflection from the mirror 16, and another portion of the collimated light to the first end 18a of the signal arm 18 in order to illuminate the tissue 20 under investigation. While some of the light provided by the signal arm is reflected and/or scattered from the surface of the tissue, at least a portion of the light enters the tissue and is scattered in different amounts at different depths within the tissue. For a tissue sample having a number of layers, the light is scattered at different depths within each of the layers and not just at the boundaries between the various layers. The light reflected by the mirror 16 is collected by the second end 14b of the reference arm 14 and the backscattered light from the tissue sample 20 is collected by the second end 18b of the signal arm 18. As shown in conjunction with the reference arm, a lens element 24 can be disposed between the second end of the reference arm and the mirror. Likewise, another lens element can be disposed between the second end of the signal arm and the tissue to facilitate the collection of the backscattered light.

The reflected light collected by the second end 14b of the reference arm 14 and the backscattered light collected by the second end 18b of the signal arm 18 are combined by the optical coupler 22 to generate an interference signal. As shown in FIG. 1, the fiberoptic interferometer 10 also includes a detector 26, such as a photodetector, for receiving the interference signal generated by the combination of reflected light and the backscattered light. Typically, the detector provides an electrical representation of the interferometric signal for subsequent storage and processing. The electrical representation provided by the detector can be either analog or digital.

To create an interferometric signal, the reflected light and the backscattered light must have traveled equal optical distances, i.e., the distance that the reflected light travels from the broadband light source 12 to the mirror 16 and finally to the optical coupler 22 must be equal to the distance that the backscattered light travels from the broadband light source to the tissue 20 and, more particularly, to the depth within the tissue at which the light is backscattered and finally to the optical coupler. In order to adjust the optical path length of the reflected light and, as a result, to create an interferometric signal based upon backscattered light which has been scattered from different corresponding depths within the tissue, the fiberoptic interferometer 10 can include adjusting means 28, such as a stepper motor, for adjusting or translating the position of the mirror relative to the second end 14b of the reference arm 14. According to this embodiment, the interferometric signal received by the detector is therefore a function of depth within the tissue. In addition, the fiberoptic interferometer can include vibrating means 30, such as for vibrating the mirror about a mean or average position in order to reduce, if not eliminate, ambient background noise superimposed upon the reflected signal.

The amount and intensity of light backscattered by a tissue sample 20 is determined by the optical properties of the tissue sample, and, more particularly, by the absorption and scattering characteristics of the tissue sample. As known to those skilled in the art, the absorption and scattering characteristics combine to define the attenuation characteristics of the tissue sample. As also known to those skilled in the art, the attenuation characteristics or attenuation coefficient of tissue of a predetermined organ generally change as a function of the wavelength of light with which the tissue is illuminated. For tissue of a predetermined organ, such as heart tissue, liver tissue or skin tissue, however, the attenuation characteristics are generally predetermined or known in advance. As such, the attenuation characteristics of tissue of a predetermined organ, such as heart tissue, can be plotted as a function of the wavelength with which the tissue is illuminated as shown in FIG. 2.

Figure 2:
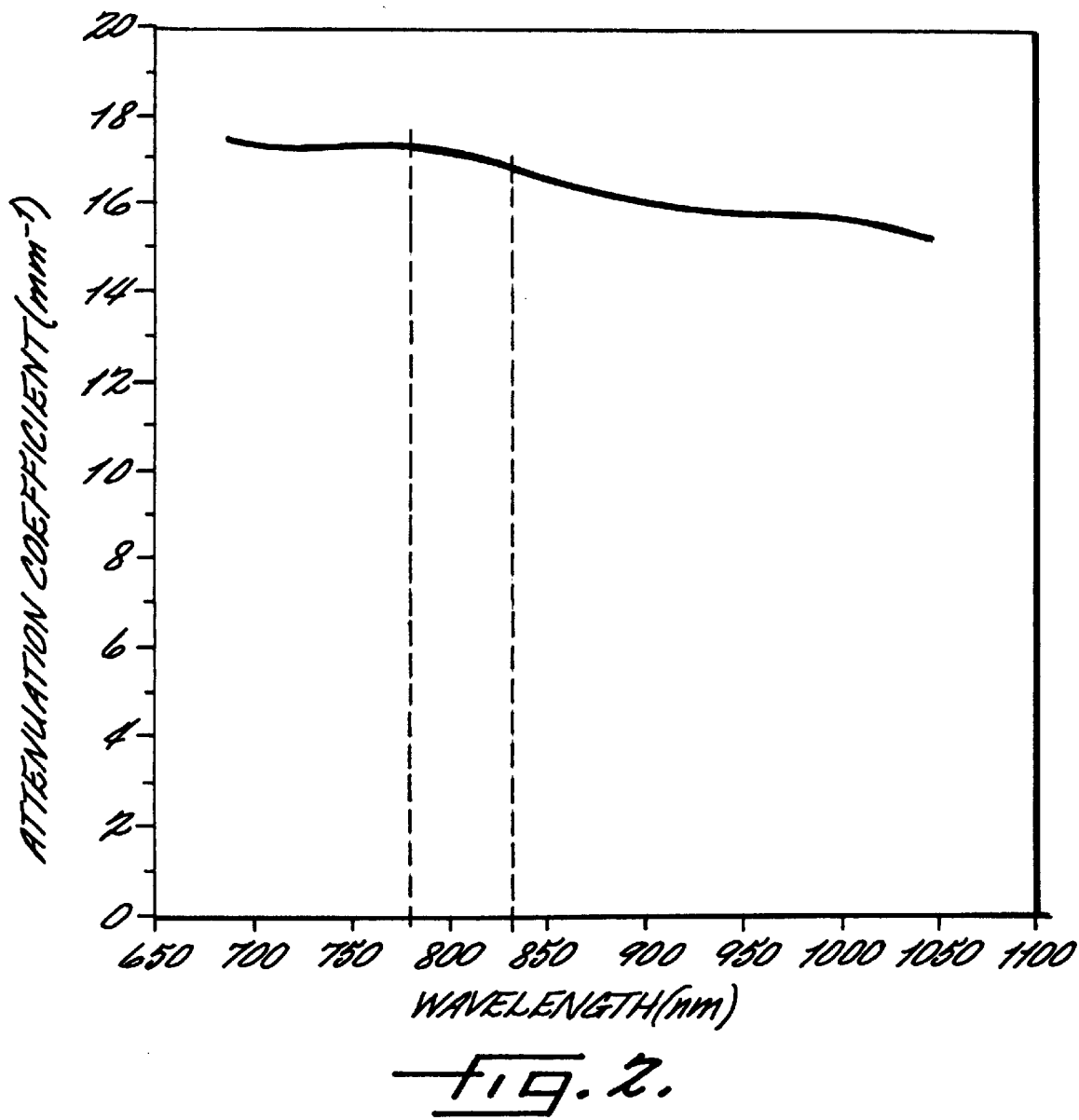
FIG. 2 represents an exemplary attenuation curve relating the attenuation coefficient of tissue of a predetermined organ, such as heart tissue, to the wavelength of light with which the tissue is illuminated.

As shown in FIG. 2, the attenuation coefficient of heart tissue generally decreases as the wavelength with which the tissue is illuminated increases. Therefore, as the wavelength with which the tissue is illuminated is increased, the light backscattered by heart tissue will typically be attenuated to a lesser degree and will make a correspondingly greater contribution to the interferometric signal received by the detector 26.

Within a predetermined range of wavelengths, the attenuation characteristics of tissue of a predetermined organ will generally define a region of minimum attenuation upon illumination of tissue of the predetermined organ with light having a first wavelength. As described above, the broadband light source 12 typically provides light having a wavelength which can vary within a predetermined range of wavelengths. For example, an SLD typically emits light having a 40 or 50 nm range of wavelengths, such as between 780 nm and 830 nm, for example. The range of wavelength emitted by a conventional SLD is depicted in FIG. 2 by the vertical lines at 780 nm and 830 nm. Within this range of wavelengths, the attenuation coefficient of tissue of the predetermined organ, such as heart tissue, generally decreases as the wavelength with which the tissue is illuminated increases. Thus, tissue of the predetermined organ will attenuate light having a wavelength of 830 nm to a lesser degree than light having shorter wavelengths. For a particular depth within a tissue sample, therefore, a greater percentage of the light having a wavelength of 830 nm will be backscattered from the tissue and collected by the detector 26 than light of the other, albeit shorter, wavelengths emitted by the broadband light source.

Since a relatively small percentage of light of any wavelength is backscattered from the various depths within a tissue sample 20, the accurate identification of a tissue sample is improved by collecting as much backscattered light as possible. Accordingly, the fiberoptic interferometer 10 and associated method of the present invention preferably analyzes the interferometric signal received by the detector 26 at the wavelength of light which contributes the most to the backscattered light. In this regard, the fiberoptic interferometer includes means 27 for comparing the interferometric signal received by the detector with predetermined interferometric signals corresponding to illumination of different types or states of tissue of the predetermined organ with light having the first wavelength, i.e., the wavelength with the lowest corresponding attenuation coefficient. Typically, the fiberoptic interferometer compares the electrical representation of the interferometric signal provided by the detector with the respective electrical representations of predetermined interferometric signals corresponding to illumination of different types or states of tissue of the predetermined organ with light having the first wavelength.

The comparing means 27 is generally embodied by a computer system having a processor or controller and an associated memory device for storing the respective electrical representations of the predetermined interferometric signals. However, the comparing means can be implemented in a variety of other fashions, including a combination of hardware and software, without departing from the spirit and scope of the present invention.

Figure 4:
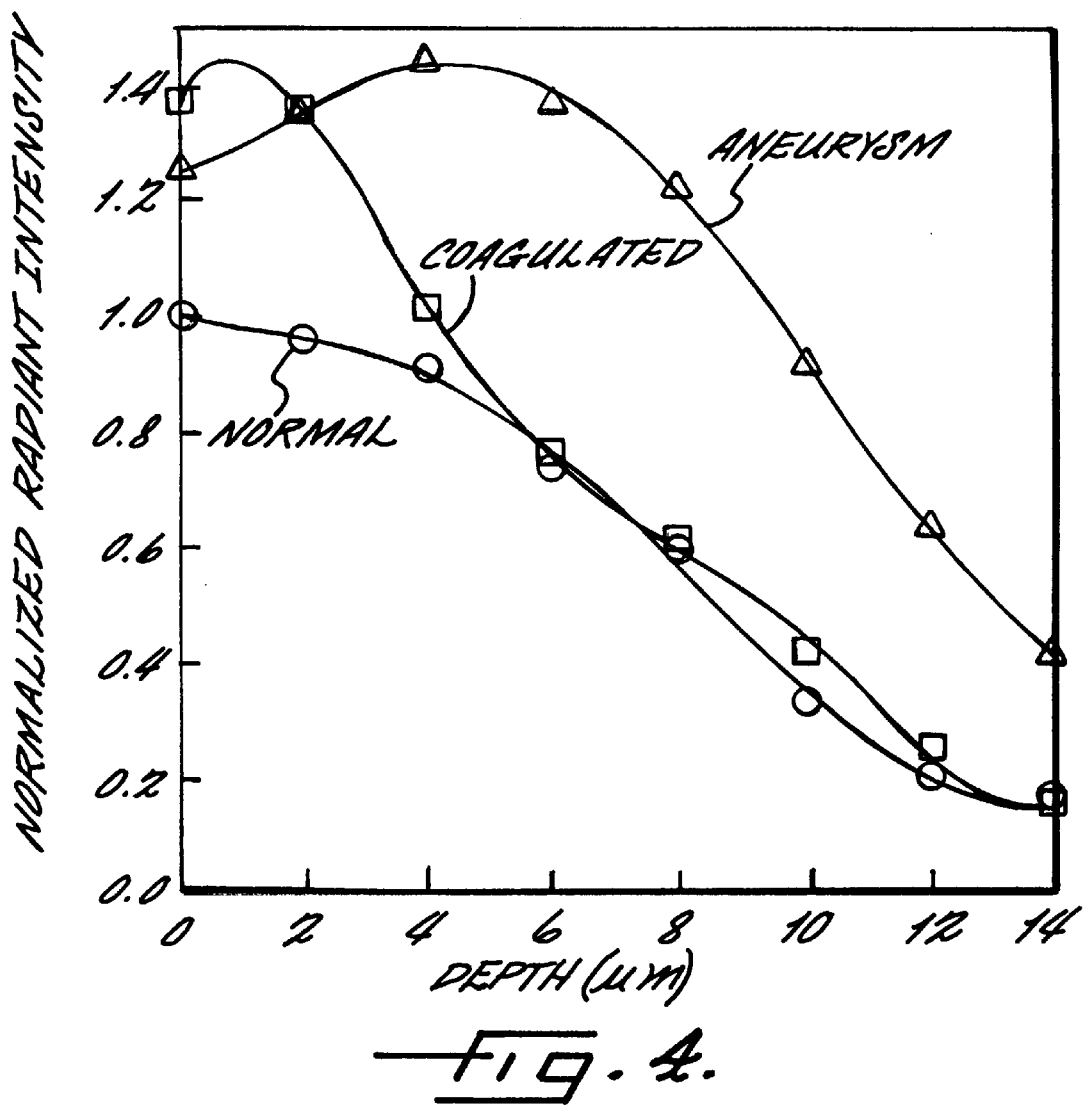
FIG. 4 is a graphical representation of the radiant intensity of backscattered light as a function of depth as measured by the fiberoptic interferometer of the present invention following irradiation of various types of heart tissue, i.e., normal, coagulated and aneurysm heart tissue, and following normalization of the intensity of the backscattered light to the intensity of light backscattered from the surface of normal heart tissue.

The predetermined interferometric signals can be defined, in advance, in a variety of manners. For example, the predetermined interferometric signals can be determined from prior analyses of tissue of the predetermined organ. With respect to heart tissue, for example, the predetermined interferometric signals can be based upon a prior analysis of normal heart tissue, coagulated heart tissue, heart aneurysm tissue and fat, as shown in FIG. 4. As illustrated, the predetermined interferometric signals can be a measure of the radiant interference intensity of the reflected and backscattered light as a function of depth within the tissue. As also shown in FIG. 4, the predetermined interferometric signals can be normalized, such as to normal or healthy tissue, if desired.

Figure 3:
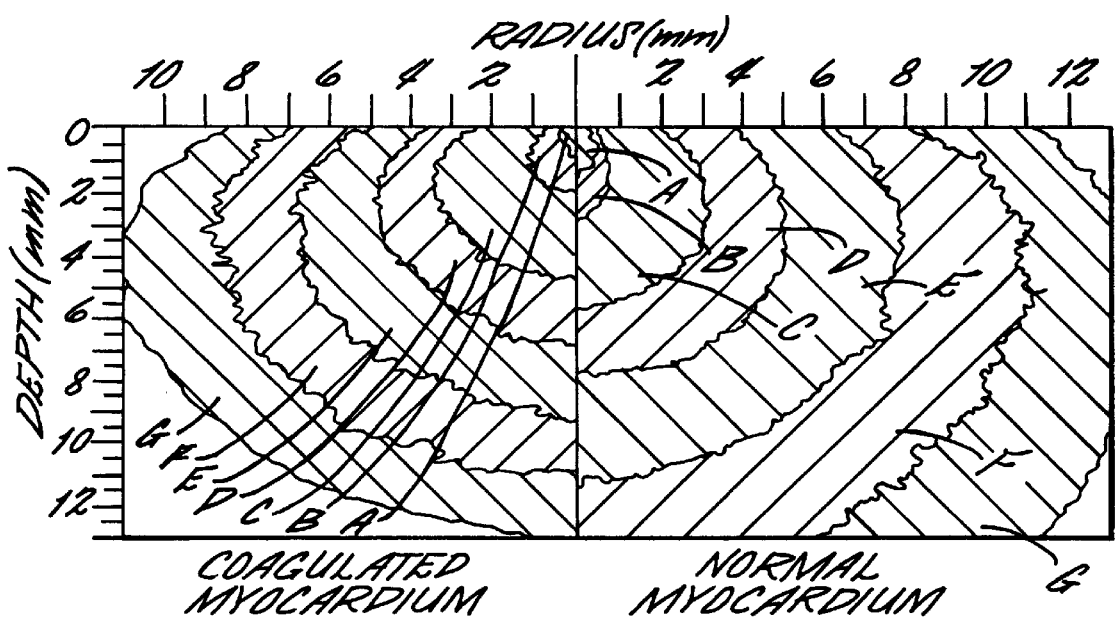
FIG. 3 is a light distribution simulation for normal and coagulated myocardium as a function of depth.

Alternatively, the predetermined interferometric signals can be based upon predefined light distribution simulations. In this regard, FIG. 3 illustrates a light distribution simulation, such as a Monte Carlo simulation, for coagulated myocardium and normal myocardium. The light distribution simulation provides a measure of the decay of light of a predetermined wavelength as a function of depth within the tissue sample. In terms of radiant energy fluent rate ($W/cm^2$) normalized based upon reflections from the surface of normal heart tissue, the various layers of heart tissue designated A, B, C, D, E, F and G have normalized radiant energy fluent rates of 1.0 $W/cm^2$, 0.1 $W/cm^2$, 0.01 $W/cm^2$, 0.003 $W/cm^2$, 0.001 $W/cm^2$, 0.0003 $W/cm^2$ and 0.0001 $W/cm^2$, respectively. This measure of the decay of light as a function of depth within a tissue is therefore a unique feature of the particular tissue, including the type or state of the tissue, and the wavelength of light emitted by the broadband light source 12. The light distribution simulations are generally computer generated based upon the irradiation of tissue having predetermined optical properties with light having a predetermined wavelength. The predetermined optical properties, such as attenuation, are generally selected so as to model tissue of a predetermined organ in a particular state. In this regard, the light distribution simulations for tissue of a predetermined organ, such as heart tissue, that is of a particular type or state, such as normal or coagulated, can be compared to the interferometric signal received by the detector 26 in response to the reflected and backscattered light in order to determine the type or state of the tissue sample at different depths therein. With respect to heart tissue, for example, the light distribution simulations for various types of heart tissue can be compared with the interferometric signal received by the detector to determine if the heart tissue is normal heart tissue, coagulated heart tissue, heart aneurysm tissue or fat for purposes of optimizing any subsequent laser irradiation of the tissue.

The comparing means 27 of the fiberoptic interferometer 10 therefore preferably includes means for identifying the predetermined interferometric signal which most closely matches the interferometric signal received by the detector 26. For example, the interferometric signal received by the detector can be compared to a database of predetermined interferometric signals and, more preferably, to the predetermined interferometric signals of the database that correspond to the illumination of various types of tissue of the predetermined organ with light having the first wavelength, i.e., the wavelength with the lowest corresponding attenuation coefficient. By identifying the predetermined interferometric signal which most closely matches the interferometric signal received by the detector, the fiberoptic interferometer can identify the type and corresponding optical properties of the tissue such that any subsequent laser irradiation of the tissue can be optimized.

For interferometric signals which can be graphically represented as a curve as shown in FIG. 4, the comparing means 27 of the fiberoptic interferometer 10 on one advantageous embodiment can identify the predetermined interferometric signal which most closely matches the interferometric signal received by the detector 26 by a least squares fit of the curves representing the respective interferometric signals. The comparing means can identify the predetermined interferometric signal which most closely matches the interferometric signal received by the detector according to other techniques, however, without departing from the spirit and scope of the present invention.

Referring lastly to FIG. 5, a schematic block diagram is provided detailing the operations performed by the fiberoptic interferometer 10 and the associated method for analyzing tissue. As shown in block 50, the broadband light source 12 is initially selected to emit light of a predetermined range of wavelengths. Within the predetermined range of wavelengths emitted by the broadband light source, the wavelength of light having the lowest corresponding attenuation coefficient, i.e., the first wavelength, is identified. See block 52. Once the broadband light source is selected, the second end 18a of the signal arm 18 is disposed in optical communication with the tissue. According to the present invention, tissue can be analyzed in vivo. Thus, the second end of the signal arm can be mounted within a probe assembly and can be inserted, typically via a catheter, into the patient's body so as to be disposed in optical communication with the tissue to be analyzed.

Once properly positioned, the broadband light source 12 then emits light having the predetermined range of wavelengths. The emitted light is split by the optical coupler 22 such that portions of the light are transmitted through both the reference arm 14 and the signal arm 18 of the fiberoptic interferometer 10. See blocks 54 and 56. While the mirror 16 is vibrated by the vibrating means 30 about an average or mean position as shown in block 58, the portion of light transmitted through the reference arm is at least partially reflected at the second end 14b of the reference arm and, more particularly, by the mirror disposed downstream of the second end of the reference arm. See block 60. Concurrently, light is at least partially scattered by the tissue 20 as shown in block 62.

As shown in block 64, the interference signal generated by the reflected light and the backscattered light is detected by detector 26 following collection by and transmission through the reference arm 14 and the sample arm 18, respectively. Based upon the reflected light and the backscattered light, the detector of this embodiment provides an electrical representation of the interferometric signal representative of the tissue 20 at the respective depth within the tissue from which the light was scattered, as shown in block 70. If the tissue sample has been completely analyzed at each of the depths of interest within the tissue sample, the comparing means 27 preferably compares the resulting interferometric signal to one or more predetermined interferometric signals representative of various types or states of tissue of the predetermined organ in order to determine the type or state of the tissue sample, such as normal, coagulated, aneurysm or fat. See blocks 66 and 72. More particularly, the comparing means compares the electrical representation of the resulting interferometric signal to one or more electrical representations of predetermined interferometric signals representative of various types or states of tissue of the predetermined organ in order to determine the type or state of the tissue sample. If the tissue sample has not been completely analyzed and portions of the tissue sample at other depths remain to be analyzed, the position of the mirror 16 is adjusted by the adjusting means 28 and the process is repeated as shown in blocks 66 and 68 of FIG. 5 in order to generate an interferometric signal representative of the tissue at another depth within the tissue.

Therefore, the fiberoptic interferometer 10 of the present invention can analyze the optical properties of tissue 20 at a variety of depths within the tissue and not just at the boundary layers of the tissue. In addition, the fiberoptic interferometer precisely determines the optical properties of the tissue by illuminating the tissue with a broadband light source 12 and by analyzing the resulting interferometric signal at the wavelength of light which is least attenuated by the tissue sample and which, therefore, contributes most to the resulting interferometric signal. In addition, the fiberoptic interferometer can determine the optical properties of the tissue based upon illumination by light of a number of different wavelengths, thereby permitting the subsequent laser treatment to be optimized by irradiating the tissue with light having a wavelength at which the tissue has the desired optical properties, such as high absorption for laser heating treatments.

While the invention has been particularly shown and described above with reference to preferred embodiments, the foregoing and other changes in form and detail may be made therein by one skilled in the art without departing from the spirit and scope of the invention.

That which is claimed:

1. A fiberoptic interferometer for analyzing a tissue of a predetermined organ, wherein tissue of the predetermined organ has predetermined attenuation characteristics which define the manner in which tissue of the predetermined organ will attenuate light of different wavelengths, the fiberoptic interferometer comprising:

a broadband light source for providing light having a wavelength within a predetermined range of wavelengths, wherein the attenuation characteristics of tissue of the predetermined organ to light having a wavelength within the predetermined range of wavelengths define a region of minimum attenuation upon illumination of tissue of the predetermined organ with light having a first wavelength;

a reference arm having a first end disposed in optical communication with said broadband light source and an at least partially reflective second end;

a signal arm having a first end disposed in optical communication with said broadband light source and a second end disposed in optical communication with the tissue such that a portion of the light provided by said broadband light source illuminates the tissue and is at least partially scattered thereby;

a detector, disposed in optical communication with the respective first ends of said reference arm and said signal arm, for receiving an interferometric signal representative of the tissue based upon light reflected by said at least partially reflective second end of said reference arm and light scattered by the tissue; and means, responsive to said detector, for individually comparing the interferometric signal received by said detector with respective ones of a plurality of predetermined interferometric signals corresponding to illumination of different types of tissue of the predetermined organ with light having the first wavelength at which the tissue of the predetermined organ creates the minimum attenuation for any wavelength of light within the predetermined range of wavelengths.

2. A fiberoptic interferometer according to claim 1 wherein said comparing means comprises means for identifying the predetermined interferometric signal which most closely matches the interferometric signal received by said detector.

3. A fiberoptic interferometer according to claim 1 wherein said detector provides an electrical representation of the interferometric signal as a function of depth within the tissue, and wherein said comparing means compares the electrical representation of the interferometric signal with predetermined electrical representations of interferometric signals corresponding to illumination of different types of tissue of the predetermined organ as a function of depth within the tissue with light having the first wavelength.

4. A fiberoptic interferometer according to claim 3 wherein said at least partially reflective second end of said reference arm is defined by a mirror, and wherein said fiberoptic interferometer further comprises mirror positioning means for controllably adjusting the position of the mirror relative to the first end of said reference arm such that the spacing therebetween is correspondingly varied.

5. A fiberoptic interferometer according to claim 4 wherein said detector provides the electrical representation of the interferometric signal representative of the tissue at different depths based upon light reflected by said mirror at different positions and light scattered by the tissue at the different depths within the tissue which correspond to the different positions of said mirror.

6. A fiberoptic interferometer according to claim 4 further comprising vibration means for vibrating said mirror about an average position to reduce ambient background noise superimposed upon the interferometric signal received by said detector.

7. A fiberoptic interferometer according to claim 1 wherein said reference arm and said signal arm comprise respective single mode optical fibers.

8. A method of analyzing a tissue of a predetermined organ, wherein tissue of the predetermined organ has predetermined attenuation characteristics which define the manner in which tissue of the predetermined organ will attenuate light of different wavelengths, the method comprising the steps of:

selecting a broadband light source for providing light having a wavelength within a predetermined range of wavelengths, wherein said selecting step comprises selecting the broadband light source such that the attenuation characteristics of tissue of the predetermined organ to light having a wavelength within the predetermined range of wavelengths define a region of minimum attenuation upon illumination of tissue of the predetermined organ with light having a first wavelength;

transmitting respective portions of the light provided by the broadband light source through a reference arm having first and second ends and a signal arm of an interferometer, wherein the portion of the light transmitted via the reference arm is at least partially reflected by the second end thereof, and wherein the portion of the light transmitted via the signal arm is at least partially scattered by the tissue;

generating an interferometric signal representative of the tissue based upon light reflected by the second end of the reference arm and light scattered by the tissue; and comparing the interferometric signal resulting from said generating step with predetermined interferometric signals corresponding to illumination of different types of tissue of the predetermined organ with light having the first wavelength, wherein said comparing step comprises identifying the predetermined interferometric signal which most closely matches the interferometric signal resulting from said generating step.

9. A method of analyzing a tissue of a predetermined organ according to claim 8 wherein said generating step comprises generating an interferometric signal as a function of depth within the tissue, and wherein said comparing step comprises compares the interferometric signal resulting from said generating step with predetermined interferometric signals corresponding to illumination of different types of tissue of the predetermined organ as a function of depth within the tissue with light having the first wavelength.

10. A method of analyzing a tissue of a predetermined organ according to claim 9 wherein the second end of the reference arm is defined by a mirror, and wherein the method further comprises the step of controllably adjusting the position of the mirror relative to the first end of the reference arm, prior to said transmitting step, such that the spacing therebetween is correspondingly varied.

11. A method of analyzing a tissue of a predetermined organ according to claim 10 wherein said generating step comprises generating the interferometric signal representative of the tissue at different depths based upon light reflected by the mirror at different positions and light scattered by the tissue at the different depths within the tissue which correspond to the different positions of the mirror.

12. A method of analyzing a tissue of a predetermined type according to claim 10 further comprising the step of vibrating the mirror about an average position to reduce ambient background noise superimposed upon the generated interferometric signal.

13. A method of analyzing tissue comprising the steps of:

providing a light source capable of emitting light of a plurality of wavelengths within a continuous spectrum;

selecting respective ones of the plurality of predetermined wavelengths of light to be emitted by the light source;

transmitting respective portions of the emitted light through a reference arm having first and second ends and a signal arm of an interferometer;

at least partially reflecting the portion of the light transmitted via the reference arm from the second end thereof;

at least partially scattering the portion of the light transmitted via the signal arm from the tissue;

generating an interferometric signal representative of the optical properties of the tissue at each of the selected wavelengths of light based upon light reflected by the at least partially reflective second end of the reference arm and light scattered by the tissues;

individually comparing the generated interferometric signals with respective ones of a plurality of predetermined interferometric signals representative of different types of tissue of the predetermined organ; and selecting light of at least one of the plurality of predetermined wavelengths for subsequent treatment of the tissue based upon the optical properties of the tissue at each of the selected wavelengths of light as represented by the respective interferometric signals.

14. A method of analyzing a tissue according to claim 13 wherein the second end of the reference arm is defined by a mirror, and wherein the method further comprises the step of controllably adjusting the position of the mirror relative to the first end of the reference arm, prior to said transmitting step, such that the spacing therebetween is correspondingly varied.

15. A method of analyzing a tissue according to claim 14 wherein said generating step comprises generating an interferometric signal representative of the optical properties of the tissue at different depths based upon light reflected by the mirror at different positions and light scattered by the tissue at the different depths within the tissue which correspond to the different positions of the mirror.

16. A method of analyzing a tissue according to claim 14 further comprising the step of vibrating the mirror about an average position to reduce ambient background noise superimposed upon the generated interferometric signal.

* * * * *